United States Patent

Kawahara et al.

Patent Number: 5,587,464
Date of Patent: Dec. 24, 1996

[54] PROCESS FOR PRODUCING DIAZOMETHANE DERIVATIVES

[75] Inventors: Ichiro Kawahara, Tokushima; Isao Wada, Naruto; Michio Sasaoka, Tokushima, all of Japan

[73] Assignee: Otsuka Kagaku Kabushiki Kaisha, Osaka, Japan

[21] Appl. No.: 501,090

[22] PCT Filed: Dec. 16, 1994

[86] PCT No.: PCT/JP94/02124

§ 371 Date: Aug. 14, 1995

§ 102(e) Date: Aug. 14, 1995

[87] PCT Pub. No.: WO95/16666

PCT Pub. Date: Jun. 22, 1995

[30] Foreign Application Priority Data

Dec. 17, 1993 [JP] Japan ................................. 5-318495

[51] Int. Cl.⁶ .............................................. C07C 245/14
[52] U.S. Cl. .......................................... 534/558; 534/565
[58] Field of Search ...................................... 534/565, 558

[56] References Cited

U.S. PATENT DOCUMENTS 4,083,837  4/1978  Gallagher et al. ............... 534/565 X
4,092,306  5/1978  Eastlick ............................ 534/565 X

OTHER PUBLICATIONS

Adamson et al., J. Chem. Soc., Perkin Trans. I, 2030–2033 (1975).

*Primary Examiner*—Fiona T. Powers
*Attorney, Agent, or Firm*—Larson & Taylor

[57] ABSTRACT

A process for producing a diazomethane derivative by oxidizing a hydrazone derivative in a two-phase system containing: a) an aqueous solution of a mixture of a caustic alkali and an alkali metal hypochlorite in respective concentrations of 4–14 w/w % and 3–10 w/w % based on the total weight of the solution; b) a hydrophobic organic solvent; c) an inorganic iodine compound, and d) a phase-transfer catalyst.

18 Claims, No Drawings

PROCESS FOR PRODUCING DIAZOMETHANE DERIVATIVES

This application is a 371 of PCT/JP94/02124 filed Dec. 16, 1994.

TECHNICAL FIELD

The present invention relates to a process for producing diazomethane derivatives.

BACKGROUND ART

Diazomethane derivatives represented by the general formula (1)

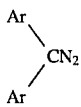

$$\begin{array}{c} Ar \\ \phantom{Ar}\diagdown \\ \phantom{Ar}\phantom{xx}CN_2 \\ \phantom{Ar}\diagup \\ Ar \end{array} \quad (1)$$

wherein Ar represents an aryl group which may be substituted are compounds useful as protective reagents for carboxyl groups contained in organic compounds.

Heretofore, the diazomethane derivatives represented by the general formula (1) are prepared from hydrazone derivatives represented by the general formula (2)

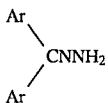

$$\begin{array}{c} Ar \\ \phantom{Ar}\diagdown \\ \phantom{Ar}\phantom{xx}CNNH_2 \\ \phantom{Ar}\diagup \\ Ar \end{array} \quad (2)$$

wherein Ar is as defined above, for example, by processes (A) to (C) described below.

(A) A process which employs a metal oxide such as mercury oxide (Journal of Organic Chemistry, 24, 560, 1959), silver oxide (Journal of Organic Chemistry, 19, 718, 1954), nickel peroxide (Journal of Chemical Society, Chemical Communication, 20, 730, 1966), manganese dioxide (Japanese Examined Patent Publication No. 13222/1991), or the like.

(B) A process which employs an organic peroxide such as peracetic acid (Japanese Examined Patent Publication No. 34701/1984), m-chloroperbenzoic acid (Japanese Examined Patent Publication No.34701/1984, Indian Journal of Chemistry, 20B, 699, 1981), or the like.

(C) A process which employs an oxidizing agent other than those described above, such as hydrogen peroxide (Japanese Examined Patent Publication No. 34701/1984 and Japanese Examined Patent Publication No. 21942/1986), an N-substituted amine halide (Japanese Unexamined Patent Publication No. 170146/1984), or the like.

However, the above processes (A) to (C) have various drawbacks.

That is to say, process (A) has the problem of environmental pollution associated with the disposal of the metal oxide and the problem that even when the metal oxide is regenerated for re-use, a lot of attention must be paid for maintaining the activity thereof. Process (B) has the drawback that the organic peroxides themselves are expensive, in addition to the problem in safety and the disposal such as removal of organic acids formed after the reaction. Process (C) has the problem in safety and the drawback that water is inevitably produced upon oxidation and lowers the concentration of hydrogen peroxide, resulting in a reduced reaction rate, and also entails the drawback that when said concentration is maintained in order to avoid said drawback by adding hydrogen peroxide, a considerably excess amount of hydrogen peroxide is required. Thus, in any of the above processes (A) to (C), consideration is necessary from a commercial viewpoints, and therefore these processes are not industrially advantageous.

On the other hand, a method is also known wherein the diazomethane derivatives obtained by the above-indicated methods is isolated and purified as crystals (Japanese Unexamined Patent Publication No. 11450/1985). However, the diazomethane derivatives are generally unstable to heat, and therefore they are used in the form of a solution as protective reagents. In this case, in addition to the yield, it is important to consider how to produce diazomethane derivatives of high purity, namely to consider how to suppress the formation of by-products such as azine compounds, which are usually formed during the production of the diazomethane derivatives.

Incidentally, Japanese Examined Patent Publication No. 34701/1984 and Journal of Chemical Society, Perkin I, 2030, 1975 disclose that when hydrazone derivatives are oxidized using an oxidizing agent such as an organic peracid, N-chlorosuccinimide, chloramine-T, hydrogen peroxide or the like, the oxidation is conducted in the presence of a phase transfer catalyst and an inorganic iodine compound under basic conditions. In these publications, there is a suggestion that sodium hypochlorite is an oxidizing agent.

However, in Japanese Examined Patent Publication No. 34701/1984, there is no working example in which sodium hypochlorite is used. In this publication, bases are merely used for the purpose of neutralizing acids such as acetic acid, which are formed when an organic acid such as peracetic acid is used.

On the other hand, Journal of Chemical Society, Perkin I, 2030, 1975 discloses a method which employs sodium hypochlorite and iodine $I_2$. However, the yield is as low as 13% as shown in Table 4 on page 2032, and therefore it is set forth on page 2032, right column, lines 16–18 of this publication that in view of such a low yield, sodium hypochlorite is not suitable as an oxidizing agent.

Subsequently, concerning the use of hydrogen peroxide as an oxidizing agent, Japanese Examined Patent Publication No. 21942/1986 discloses a process in which the oxidation is conducted in the presence of an alkali metal carbonate and in the presence of a phase transfer catalyst and an inorganic iodine compound, while maintaining the concentration of hydrogen peroxide in the reaction system at 20% or higher. However, the yield of the product is 90% and still insufficient, and furthermore the diazomethane derivative of high purity is not obtained.

DISCLOSURE OF THE INVENTION

From a standpoint of industrial production of diazomethane derivatives, the inventors of this invention conducted an extensive research on a process for obtaining in a large amount the diazomethane derivatives in high yield and in high purity. In the course of the research, the inventors conceived using, as the oxidizing agent, alkali metal hypochlorites, such as sodium hypochlorite, which are most inexpensive as industrial raw material, highly safe and easy to react and which involves very easy disposal of the waste water.

In accordance with the research of the present inventors, however, when the alkali metal hypochlorite is used as the oxidizing agent, the reaction conducted following the teachings of the above prior art entails the problem that the yield and/or the reaction selectivity are/is lowered and that the by-products such as azine compounds are formed, and thus it was not possible to obtain the diazomethane derivatives of high purity and in high yields.

As a result of further researches conducted by the inventors, however, it has been found that among the four factors which are an alkali metal hypochlorite, a base, an inorganic iodine compound and a phase transfer catalyst, the concentration of the base and the concentration of the alkali metal hypochlorite mutually influence the yield and the reaction selectivity in the oxidizing agent aqueous solution, i.e., a mixed aqueous solution of the base and the alkali metal hypochlorite, and that the yield and the reaction selectivity (purity of the diazomethane derivative) are both significantly improved by selecting certain ranges of the concentrations of the base and the alkali metal hypochlorite. The present invention has been accomplished based on these findings.

Thus, the present invention provides a process for producing a diazomethane derivative represented by the general formula (1), characterized in that the hydrazone derivative represented by the general-formula (2) is oxidized in a two-phase system comprising (a) a mixed aqueous solution containing, based on the total weight of the mixed aqueous solution, 4 to 14 w/w % of a caustic alkali and 3 to 10 w/w % of an alkali metal hypochlorite, (b) a hydrophobic organic solvent, (c) an inorganic iodine compound, and (d) a phase transfer catalyst.

In this specification, examples of the aryl groups contained in the aryl group which may be substituted, as represented by Ar, are a phenyl group, a naphthyl group and so on.

Examples of the substituent or substituents which may substitute the aryl groups represented by Ar include a halogen atom (fluorine atom, chlorine atom, bromine atom, iodine atom, etc.), a nitro group, a cyano group, an aryl group (phenyl group, naphthyl group, etc.), a lower alkyl group, especially an alkyl group having 1 to 6 carbon atoms (such as methyl group, ethyl group, propyl group, isopropyl group, butyl group, sec-butyl group, tert-butyl group, etc.), a lower alkoxy group, especially an alkoxy group having 1 to 6 carbon atoms (such as methoxy group, ethoxy group, propyloxy group, etc.). Aryl groups represented by Ar may be substituted by 1 to 5, preferably 1 to 2, identical or different substituents selected from the group consisting of the above-mentioned a halogen atom, a nitro group, a cyano group, an aryl group, a lower alkyl group and a lower alkoxy group.

Among the above-mentioned substituted aryl groups represented by Ar, preferred are a phenyl group substituted with one or two halogen atoms, a phenyl group substituted with one or two nitro groups, a phenyl group substituted with one or two cyano groups, a phenyl group substituted with one or two aryl groups, a phenyl group substituted with one or two lower alkyl groups, and a phenyl group substituted with one or two lower alkoxy groups.

In particular, Ar is preferably an unsubstituted phenyl group.

The hydrazone derivatives represented by the general formula (2) used as the starting material of the process of the present invention are known compounds or can be easily prepared according to known methods.

Alkali metal hypochlorites used in the process of the present invention can be readily prepared by introducing chlorine to an aqueous solution of an alkali metal hydroxide. Particularly, sodium hypochlorite is preferred. Generally, sodium hypochlorite is inexpensively and readily available as an industrial raw material in the form of an aqueous sodium hypochlorite solution having a concentration of 12 to 14 w/w %, calculated as effective chlorine (as $Cl_2$), and therefore it is preferable to use such solution as it is or as diluted with water.

The amount of the alkali metal hypochlorite (especially, sodium hypochlorite) to be used is usually in the range of 1 to 5 moles, preferably 1 to 2 moles, per mole of the hydrazone derivative represented by the general formula (2). In order to achieve a yield and a reaction selectivity (purity of the diazomethane derivative) of 96% or higher, it is important that the concentration of the alkali metal hypochlorite in the mixed aqueous solution of the caustic alkali and the alkali metal hypochlorite be in the range of 3 to 10 w/w %, preferably in the range of 4 to 8 w/w %, relative to the total weight of said mixed aqueous solution.

On the other hand, as the caustic alkali, conventionally known caustic alkalis are usable, including alkali metal hydroxides such as lithium hydroxide, sodium hydroxide and potassium hydroxide. Sodium hydroxide is economically advantageous and preferable. Considering the ease of handling, it is generally advantageous to use the caustic alkali in the form of an aqueous solution. In the present invention, it is preferable to admix an aqueous solution of the caustic alkali in advance with an aqueous solution of an alkali metal hypochlorite in such a manner that the caustic alkali is present at a concentration in the above-specified concentration range and to use the resulting mixed solution.

The amount of the caustic alkali to be used is usually in the range of 1 to 10 moles, per mole of the hydrazone derivative represented by the general formula (2). Considering the neutralization in the work-up step after the reaction, the caustic alkali is preferably used in an amount of 5 mole or less, particularly about 1.2 to about 5 moles, per mole of the hydrazone derivative. In order to achieve the yield and the reaction selectivity of 96% or higher, it is important that the concentration of the caustic alkali in the mixed aqueous solution of the caustic alkali and the alkali metal hypochlorite be in the range of 4 to 14 w/w %, preferably in the range of 5 to 12 w/w %.

In the process according to the present invention, it is essential to conduct the reaction in a two-phase system composed of a hydrophobic organic solvent and the above mixed aqueous solution of the caustic alkali and the alkali metal hypochlorite, namely, in a two-phase system of an organic solvent-water mixture.

As the hydrophobic organic solvent, a wide range of conventionally known hydrophobic organic solvents can be used insofar as they are inert to the oxidation reaction. Examples of the hydrophobic organic solvents include chlorinated hydrocarbons, especially chlorinated hydrocarbons having 1 to 4 carbon atoms and substituted with 1 to 4 chlorine atoms (specifically, dichloromethane, 1,2-dichloroethane, chloroform, etc.); aliphatic esters, especially esters of a $C_1$–$C_4$ fatty acid and a $C_1$–$C_4$ alcohol (specifically, ethyl acetate, butyl acetate, etc.); ethers, especially di($C_1$–$C_4$ alkyl)ethers (specifically, diethyl ether, diisopropyl ether, etc.); aliphatic hydrocarbons, especially straight- or branched-chain or alicyclic aliphatic hydrocarbons having 5 to 8 carbon atoms (specifically, n-hexane, cyclohexane, etc.); aromatic hydrocarbons (specifically, benzene, toluene, etc.); and so on. These solvents may be used singly or at least two of them may be used in admixture.

Among these hydrophobic organic solvents, the chlorinated hydrocarbon solvents, especially dichloromethane, are preferred in respect of its ability to dissolve the starting hydrazone derivative and the desired diazomethane derivative as well as safety and economy.

While the concentration of the hydrazone derivative represented by the formula (2) relative to the hydrophobic organic solvent is not particularly limited, they are usually in the range of about 10 to about 150 w/v %, preferably about 15 to about 100 w/v %, especially in view of handling amenability, especially considering the ease of liquid separation after the reaction. Herein, w/v % is expressed by the following formula:

$$(w_1/v_1) \times 100$$

wherein $v_1$ is the volume (ml) of the hydrophobic organic solvent used and $w_1$ is the amount (g) of the hydrazone derivative represented by the general formula (2).

According to the present invention, the reaction is conducted in a two-phase system as described above. As far as the hydrophobic organic solvent (organic layer) and the mixed aqueous solution of a caustic alkali and an alkali metal hypochlorite (aqueous layer) in the reaction system form a two-phase system, the ratio of the amount of the organic layer to the amount of the aqueous layer can be suitably selected from a wide range. Generally, the above mixed aqueous solution is preferably used in a volume of about 1 to 5 times the volume of the hydrophobic organic solvent.

In the present invention, as the inorganic iodine compound, a wide range of conventionally known inorganic iodine compounds can be mentioned, such as iodine, alkali metal salts of metaperiodic acid (specifically, sodium metaperiodate and potassium metaperiodate), alkali metal salts of hydrogen iodide (specifically, sodium iodide and potassium iodide), quaternary ammonium salts of iodide (specifically, ammonium iodide, tetramethylammonium iodide, tetraethylammonium iodide, tetrabutylammonium iodide), and so on. These may be used singly or at least two of them may be used in admixture. Among these, the alkali metal salts of hydrogen iodide are preferably used.

The reaction of the present invention may proceed even in the absence of the inorganic iodine compound, but generally the reaction tends to proceed slowly and the starting material tends to remain unreacted. Therefore, the amount of the inorganic iodine compound to be used is preferably in the range of 0.001 to 1 mole per mole of the hydrazone derivative represented by the general formula (2), and more preferably in the range of 0.01 to 0.1 mole from the standpoint of reaction rate and economy. It is also preferable that the inorganic iodine compound be added to the solution of the hydrazone derivative represented by the general formula (2) in the hydrophobic organic solvent.

On the other hand, as the phase transfer catalyst, a wide range of conventionally known phase transfer catalysts can be used. Examples of the phase transfer catalysts are quaternary ammonium salts, such as tetramethylammonium chloride, tetrabutylammonium chloride, benzyldimethyloctylammonium chloride, benzyltrioctylammonium chloride, tetrabutylammonium hydrogen sulfate, tetrabutylammonium hydroxide, etc.; crown ethers such as 15-crown-5, 18-crown-6, etc.; polyethers such as polyethylene glycol, etc.; polyoxyethylene sorbitan fatty acid esters (tradename: "Tween 80", etc.); and so on. These may be used singly or at least two of them may be used in admixture. Among these, the quaternary ammonium salts are particularly preferred.

The amount of the phase transfer catalyst to be used is usually in the range of 0.0001 to 50 w/w % relative to the hydrazone derivative represented by the general formula (2).

In order to obtain the diazomethane derivatives in high yields and in high purity, it is the most preferable to use the phase transfer catalyst in the range of 0.001 to 3 w/w % relative to the hydrazone derivative.

In other words, the reaction of the present invention can proceed even in the absence of a phase transfer catalyst. However, without using the phase transfer catalyst, the diazomethane derivative decomposes during and after the reaction, giving large amounts of by-products such as carbonyl compounds and the like, and resulting in a significant decrease in the yield and purity of the diazomethane derivatives. Therefore, the phase transfer catalyst is indispensable. Also the use of the phase transfer catalyst in excess of the above-indicated amount results in the decrease in the yield and purity, so that the diazomethane derivatives cannot be obtained in a satisfactory manner. Thus, the amount of the phase transfer catalyst used is preferably as small as possible.

According to the present invention, the phase transfer catalyst may be contained either in the hydrophobic organic solvent phase or in the mixed aqueous solution phase of a caustic alkali and an alkali metal hypochlorite, or may be contained in both of these phases.

When the phase transfer catalyst is added to the mixed aqueous solution phase of a caustic alkali and an alkali metal hypochlorite, if the phase transfer catalyst is low in solubility in the mixed aqueous solution and if the specific gravity thereof is less than that of the above mixed aqueous solution, the phase transfer catalyst cannot be substantially dissolved in the mixed aqueous solution beyond the saturation concentration and is present as separated in the upper phase. Therefore, the phase transfer catalyst may be used in excess of the above-specified amount.

The reaction of the present invention can be conducted in various manners. Generally, the reaction is preferably conducted by adding in small amounts, e.g., dropwise, with stirring, a mixed aqueous solution of a caustic alkali and an alkali metal hypochlorite to a mixture comprising a hydrophobic organic solvent, a hydrazone derivative represented by the general formula (2), an inorganic iodine compound and a phase transfer catalyst (hydrophobic organic solvent layer). The phase transfer catalyst may be added to the above mixed aqueous solution.

Alternatively, the reaction of the present invention may be conducted by adding in small amounts, e.g., dropwise, with stirring, a mixture comprising a hydrophobic organic solvent, a hydrazone derivative represented by the general formula (2), an inorganic iodine compound and a phase transfer catalyst to a mixed aqueous solution of an caustic alkali and an alkali metal hypochlorite. The phase transfer catalyst may be added to the above mixed aqueous solution.

The reaction of the present invention takes place during the above dropwise addition. Since the reaction is an exothermic reaction, the temperature of the reaction system increases as the dropwise addition is conducted. Thus, the reaction is preferably conducted with the temperature of the reaction system maintained within a certain range.

In general, the reaction of the present invention proceeds at a temperature of from −30° to 50° C. When the temperature is above 50° C., the diazomethane derivative tends to decompose. In order to obtain diazomethane derivatives of higher purity, the reaction is preferably performed at a temperature in the range of −20° to 30° C.

As described above, the reaction of the present invention generates heat by the dropwise addition of the aqueous solution of the caustic alkali and the alkali metal hypochlorite to the hydrophobic organic solvent layer (or by the addition in a reversed manner), and therefore, it is advantageous to maintain the temperature at a lower range during the initial stage of the reaction. To this end, it is preferable to cool beforehand the hydrophobic organic solvent layer as well as the mixed aqueous solution of a caustic alkali and an alkali metal hypochlorite, prior to the reaction.

The pressure in the reaction system is preferably adjusted to an atmospheric pressure, but it may be a reduced pressure or an elevated pressure.

The speed of the dropwise addition of the mixed aqueous solution of a caustic alkali and an alkali metal hypochlorite or the speed of the dropwise addition of the hydrophobic organic solvent layer are not particularly limited, insofar as the reaction temperatures are maintained within the above range. Usually, it is preferable to conduct the addition over a time period in the range of 0.1 to 8 hours.

In order to complete the reaction sufficiently, stirring is preferably continued for additional 5 to 60 minutes at the above reaction temperature, after completion of the dropwise addition.

Since the reaction of the present invention is effected in a two-phase heterogeneous system, particular attention should be paid to the stirring efficiency. That is to say, when the layer of hydrophobic organic solvent and the layer of the mixed aqueous solution of a caustic alkali and an alkali metal hypochlorite cannot be admixed sufficiently, reaction efficiency (yield) and reaction selectivity (purity of the diazomethane derivative) will decrease, and therefore it is preferable to select a suitable stirring method and suitable stirring speed capable of sufficiently mixing the two phases.

Such stirring may be carried out by using a known stirring device which is conventionally used for effecting this type of reaction in a two-phase system.

The hydrophobic organic solvent solution containing the diazomethane derivative represented by the general formula (1) obtained by the above method, when simply separated, has a purity sufficient to be used as a protective reagent for carboxyl groups contained in organic compounds, and is therefore usable as such. It is also possible to use the diazomethane derivative after isolated as crystals by evaporating a portion of the organic solvent at a low temperature.

EXAMPLES

The following examples are provided to illustrate this invention in further detail. Analysis of the diazomethane derivatives was conducted using the liquid chromatography (HPLC) technique, since the conventional UV analysis cannot detect the impurities formed as by-products and therefore the yield and purity of the diazomethane derivatives quantified thereby is greater than the actual ones.

In the following Examples and Comparative Examples, "%" means "% by weight, i.e., w/w %" unless otherwise indicated.

Example 1

To 180 ml of water were added 267 ml of a 25% aqueous solution of sodium hydroxide (NaOH 2.13 moles) and 241 ml of an aqueous solution of sodium hypochlorite (NaOCl 0.57 mole) having 13.8% of effective chlorine, to thereby prepare a mixed aqueous solution containing 10.4 w/w % of sodium hydroxide and 5.2 w/w % of sodium hypochlorite. The mixed aqueous solution thus obtained was ice-cooled with stirring.

On the other hand, 89.0 g (0.45 mole) of benzophenone hydrazone (BPH) was dissolved in 190 ml of dichloromethane. To this solution were added 0.10 ml of a 50% aqueous solution of benzyldimethyloctylammonium chloride (trade name: "QBA-811" produced by Takemoto Yushi Kabushiki Kaisha) (benzyldimethyloctylammonium chloride 0.05 g) and an aqueous solution of potassium iodide (KI 4.5 g (0.03 mole)/water 6 ml), and the resulting mixture was ice-cooled with stirring.

After it was confirmed that the temperatures of both of the solutions became 5° C. or lower, the aqueous solution of the oxidizing agent prepared above was gradually added dropwise to the solution of benzophenone hydrazone in dichloromethane over 2 hours in such a manner that the temperature of reaction system was maintained at 0° to 20° C. After the dropwise addition was completed, the mixture as such was vigorously agitated for another 10 minutes. After allowing the mixture to stand for 30 minutes, the dichloromethane layer was separated.

HPLC analysis revealed that this dichloromethane layer contained 86.5 g of diphenyldiazomethane (Yield 98%), 0.8 g of benzophenone (Yield 0.9%) and 0.6 g of benzophenone azine (Yield 0.8%). The content of the diphenyldiazomethane was calculated to be 90.90 g (Yield 103%) when determined by the UV analysis.

Example 2

To 90 ml of water were added 134 ml of a 25% aqueous solution of sodium hydroxide (NaOH 1.07 moles) and 121 ml of an aqueous solution of sodium hypochlorite (NaOCl 0.29 mole) having 13.8% effective chlorine, to thereby give a mixed aqueous solution containing 10.4 w/w % sodium hydroxide and 5.2 w/w % sodium hypochlorite. To this solution, 0.10 ml of a 50% aqueous solution of benzyldimethyloctylammonium chloride (benzyldimethyloctylammonium chloride 0.05 g) was added, and the resulting mixture was ice-cooled with stirring.

On the other hand, 44.5 g (0.23 mole) of benzophenone hydrazone was dissolved in 95 ml of dichloromethane, to which was added an aqueous solution of potassium iodide (potassium iodide 2.25 g (0.015 mole)/water 3 ml) and the resulting mixture was ice-cooled with stirring.

After confirming that the temperatures of both solutions became 5° C. or less, the aqueous solution of the oxidizing agent prepared above was gradually added dropwise to the solution of benzophenone hydrazone in dichloromethane over 1 hour in such a manner that the temperature of reaction system was maintained at 0° to 20° C. After the dropwise addition was completed, the mixture was agitated for another 10 minutes. After 30 minutes of standing, the dichloromethane layer was separated.

HPLC analysis revealed that this dichloromethane layer contained 44.0 g of diphenyldiazomethane (quantitative yield).

Examples 3 to 12

Reactions were performed under the same conditions as in Example 2 except that the amounts of water, the 25% aqueous solution of sodium hydroxide, the 50% aqueous solution of benzyldimethyloctylammonium chloride and the dichloromethane used were changed as shown in Table 1. The results are summarized in Table 1.

TABLE 1

| Example | MDC | QBA-811 | NaOH | Water | DDM | BP | BPA |
|---------|-----|---------|------|-------|-----|-----|-----|
| 3 | 95 ml | 1.88 ml (0.94 g) | 134 ml | 90 ml | 98% | 0.8% | 0.8% |
| 4 | 95 ml | 0.50 ml (0.25 g) | 134 ml | 90 ml | 99% | 0.6% | 0.4% |
| 5 | 95 ml | 0.02 ml (0.01 g) | 134 ml | 90 ml | quantitative | 0% | 0% |
| 6 | 95 ml | 0.05 ml (0.025 g) | 134 ml | 180 ml | 99% | 0.7% | 0.3% |
| 7 | 95 ml | 0.05 ml (0.025 g) | 114.3 ml | 115 ml | 99% | 0.7% | 0.3% |
| 8 | 95 ml | 0.05 ml (0.025 g) | 85.9 ml | 151.5 ml | 98% | 0.9% | 0.7% |
| 9 | 47.5 ml | 0.05 ml (0.025 g) | 85.9 ml | 90 ml | 98% | 0.9% | 0.8% |
| 10 | 31.5 ml | 0.05 ml (0.025 g) | 85.9 ml | 90 ml | 98% | 0.8% | 0.8% |
| 11 | 23.7 ml | 0.05 ml (0.025 g) | 85.9 ml | 90 ml | 98% | 0.9% | 0.9% |
| 12 | 47.5 ml | 0.05 ml (0.025 g) | 85.9 ml | 0 ml | 98% | 0.7% | 0.8% |

MDC: dichloromethane
QBA-811: a 50% (w/w) aqueous solution of benzyldimethyloctylammonium chloride
NaOH: a 25% (w/w) aqueous solution of sodium hydroxide
DDM: diphenyldiazomethane
BP: benzophenone
BPA: benzophenone azine

Examples 13 to 21

Reactions were performed under the same conditions as in Example 2 except that the phase transfer catalyst used was changed from benzyldimethyloctylammonium chloride to each of the catalysts shown in Table 2. The results are summarized in Table 2.

TABLE 2

| Example | phase transfer catalyst | | DDM | BP | BPA |
|---------|------------------------|--|-----|-----|-----|
| 13 | Tween 80 | 0.50 ml (0.53 g) | quantitative | 0% | 0% |
| 14 | 18-crown-6 | 0.50 g | 99% | 0.5% | 0.3% |
| 15 | 15-crown-5 | 0.50 ml (0.55 g) | 99% | 0.6% | 0.4% |
| 16 | Peg-3000 | 0.50 g | 99% | 0.6% | 0.3% |
| 17 | QBA-444 | 1.00 ml (0.50 g) | 99% | 0.5% | 0.5% |
| 18 | n-Bu$_4$NHSO$_4$ | 0.50 g | 98% | 0.8% | 0.7% |
| 19 | n-Bu$_4$NOH | 5.00 ml (0.50 g) | 98% | 0.9% | 0.8% |
| 20 | n-Bu$_4$NCl | 1.00 ml (0.52 g) | 98% | 0.8% | 0.8% |
| 21 | Me$_4$NCl | 0.50 g | 98% | 0.9% | 0.9% |

Tween 80: polyoxyethylene(20)sorbitan monooleate (produced by ICI Inc.)
Peg-3000: polyethylene glycol (average molecular weight = 3000)
QBZ-444: a 50% (w/w) aqueous solution of benzyltri-n-butylammonium chloride (produced by Takemoto Yushi Kabushiki Kaisha)
n-Bu$_4$NOH: a 10% (w/w) aqueous solution
n-Bu$_4$NCl: a 50% (w/w) aqueous solution
DDM: diphenyldiazomethane
BP: benzophenone
BPA: benzophenone azine

Comparative Example 1

Reaction was performed under the same conditions as in Example 1 except that the aqueous solution of potassium iodide (potassium iodide 4.5 g/water 6 ml) was not used, and then the dichloromethane layer was separated in the same manner as in Example 1.

HPLC analysis revealed that this dichloromethane layer contained 36.6 g of diphenyldiazomethane (Yield 42%), 1.3 g of benzophenone (Yield 1.6%), 0.1 g of benzophenone azine (Yield 0.1%) and 50.4 g of the starting benzophenone hydrazone (Yield 57%).

Comparative Example 2

Reaction was performed under the same conditions as in Example 1 except that 267 ml of water was added in place of 267 ml of the 25% aqueous solution of sodium hydroxide, and then the dichloromethane layer was separated in the same manner as in Example 1.

HPLC analysis revealed that this dichloromethane layer contained 13.6 g of diphenyldiazomethane (Yield 15%), 8.1 g of benzophenone (Yield 9.8%) and 22.7 g of benzophenone azine (Yield 27%).

Comparative Example 3

Reaction was performed under the same conditions as in Example 1 except that the 50% aqueous solution of benzyldimethyloctylammonium chloride was not used, and then the dichloromethane layer was separated in the same manner as in Example 1.

HPLC analysis revealed that this dichloromethane layer contained 48.7 g of diphenyldiazomethane (Yield 55%), 16.2 g of benzophenone (Yield 19%) and 8.2 g of benzophenone azine (Yield 10%).

Comparative Example 4

Reaction was performed under the same conditions as in Example 1 except that the amount of the 50% aqueous solution of benzyldimethyloctylammonium chloride was changed from 0.10 ml to 7.50 ml, and then the dichloromethane layer was separated in the same manner as in Example 1.

HPLC analysis revealed that this dichloromethane layer contained 77.2 g of diphenyldiazomethane (Yield 87%), 4.1 g of benzophenone (Yield 5.0%) and 4.6 g of benzophenone azine (Yield 5.6%).

Comparative Examples 5 to 8

Reactions were performed under the same conditions as in Example 2 except that the conditions as shown in Table 3 were employed. The results are summarized in Table 3.

TABLE 3

| Comparative Example | NaOH (w/w %) | Water | DDM | BPH | BP | BPA |
|---------|------|-------|-----|-----|-----|-----|
| 5 | 28.5 ml (25%) | 224 ml | 68% | 0% | 9.0% | 22% |
| 6 | 80 ml (49%) | 140 ml | 83% | 16% | 0.2% | 0.3% |
| 7 | 134 ml (25%) | 531 ml | 89% | 0% | 3.6% | 6.4% |

TABLE 3-continued

| Comparative Example | NaOH (w/w %) | Water | DDM | BPH | BP | BPA |
|---|---|---|---|---|---|---|
| 8 | 26.57 ml (49%) | 0 ml | 27% | 72% | 0.5% | 0.5% |

NaOH (w/w %): an aqueous solution of sodium hydroxide having the concentration value (w/w %) given in parentheses
DDM: diphenyldiazomethane
BPH: benzophenone hydrazone
BP: benzophenone
BPA: benzophenone azine

We claim:

1. A process for producing a diazomethane derivative represented by the general formula

  (1)

wherein Ar represents an aryl group which may be substituted, characterized in that a hydrazone derivative represented by the general formula

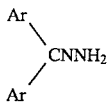  (2)

wherein Ar is as defined above is oxidized in a two-phase system comprising (a) a mixed aqueous solution containing, based on the total weight of the mixed aqueous solution, 4 to 14 w/w % of a caustic alkali and 3 to 10 w/w % of an alkali metal hypochlorite,
(b) a hydrophobic organic solvent,
(c) an inorganic iodine compound, and
(d) a phase transfer catalyst.

2. A process according to claim 1 wherein Ar is a phenyl group.

3. A process according to claim 1 wherein the alkali metal hypochlorite is sodium hypochlorite.

4. A process according to claim 1 wherein the alkali metal hypochlorite is used in an amount of 1 to 5 moles, per mole of the hydrazone derivative.

5. A process according to claim 1 wherein the caustic alkali is at least one member selected from the group consisting of lithium hydroxide, sodium hydroxide and potassium hydroxide.

6. A process according to claim 1 wherein the caustic alkali is used in an amount of 1 to 10 moles, per mole of the hydrazone derivative.

7. A process according to claim 1 wherein the hydrophobic organic solvent is at least one member selected from the group consisting of chlorinated hydrocarbons, aliphatic esters, ethers, aliphatic hydrocarbons and aromatic hydrocarbons.

8. A process according to claim 7 wherein the hydrophobic organic solvent is a chlorinated hydrocarbon.

9. A process according to claim 1 wherein the hydrazone derivative is used at a concentration of 10 to 150 w/v % relative to the hydrophobic organic solvent.

10. A process according to claim 1 wherein the inorganic iodine compound is at least one member selected from the group consisting of iodine, alkali metal salts of metaperiodic acid, alkali metal salts of hydrogen iodide and ammonium iodides.

11. A process according to claim 10 wherein the inorganic iodine compound is an alkali metal salt of hydrogen iodide.

12. A process according to claim 1 wherein the inorganic iodine compound is used in an amount of 0.001 to 1 mole per mole of the hydrazone derivative.

13. A process according to claim 1 wherein the inorganic iodine compound and the hydrazone derivative are contained in the hydrophobic organic solvent.

14. A process according to claim 1 wherein the phase transfer catalyst is at least one member selected from the group consisting of quaternary ammonium salts, crown ethers and polyethers.

15. A process according to claim 1 wherein the phase transfer catalyst is used in an amount of 0.0001 to 50 w/w % relative to the hydrazone derivative.

16. A process according to claim 1 wherein the phase transfer catalyst is used in an amount of 0.001 to 3 w/w % relative to the hydrazone derivative.

17. A process according to claim 1 wherein the oxidation is conducted at a temperature in the range of from −30° to 50° C.

18. A process according to claim 1 wherein Ar is a phenyl group, and the alkali metal hypochlorite is sodium hypochlorite and the oxidation is conducted at a temperature of from −20° to 30° C.

* * * * *